(12) United States Patent
Görtler et al.

(10) Patent No.: US 7,444,008 B2
(45) Date of Patent: Oct. 28, 2008

(54) METHOD AND COMPUTERIZED SYSTEM FOR AUTOMATICALLY PROCESSING STUDIES ACQUIRED BY AN IMAGING EXAMINATION SYSTEM

(75) Inventors: Georg Görtler, Baiersdorf (DE); Rainer Kuth, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1176 days.

(21) Appl. No.: 10/615,715

(22) Filed: Jul. 9, 2003

(65) Prior Publication Data
US 2004/0083257 A1 Apr. 29, 2004

(30) Foreign Application Priority Data
Jul. 9, 2002 (DE) ............... 102 30 878

(51) Int. Cl.
G06K 9/00 (2006.01)
G06F 19/00 (2006.01)

(52) U.S. Cl. .......................... 382/128; 705/3
(58) Field of Classification Search ................ 382/128, 382/129–132; 378/4, 98–98.12; 600/407; 705/2, 3
See application file for complete search history.

(56) References Cited

U.S. PATENT DOCUMENTS

| | | | |
|---|---|---|---|
| 5,655,084 A | 8/1997 | Pinsky et al. | |
| 5,993,001 A * | 11/1999 | Bursell et al. | 351/212 |
| 6,006,191 A * | 12/1999 | DiRienzo | 705/2 |
| 6,241,668 B1 | 6/2001 | Herzog | |
| 6,829,378 B2 * | 12/2004 | DiFilippo et al. | 382/128 |
| 7,082,440 B2 | 7/2006 | Ogino et al. | |
| 2002/0028007 A1 * | 3/2002 | Gendron et al. | 382/128 |

OTHER PUBLICATIONS

"A Distributed Architecture for Medical Instrumentation: An Electric Current Computed Tomograph," Goble et al., IEEE Engineering in Medicine and Biology Society, 10th Annual Int. Conf. (1988).

* cited by examiner

Primary Examiner—Aaron W Carter
(74) Attorney, Agent, or Firm—Schiff Hardin LLP

(57) ABSTRACT

In a method and system for automatically processing studies of imaging examination systems, each of the studies is given a priority code. Dependent on its priority code, the study is either processed immediately on a first computer allocated to the appertaining imaging examination system or the study is first intermediately stored in a memory device for a later processing, and an identifier allocated to the study is stored in a processing job list. At later points in time, the studies whose identifiers are stored in the processing job list are processed according to a predefined sequence. The first computer has further computers allocated to it for this purpose. The availability of the allocated, further computers is then checked and, insofar as one of the allocated computers is available for a processing of the study, an intermediately stored study is communicated to the appertaining, allocated computer for processing.

19 Claims, 2 Drawing Sheets

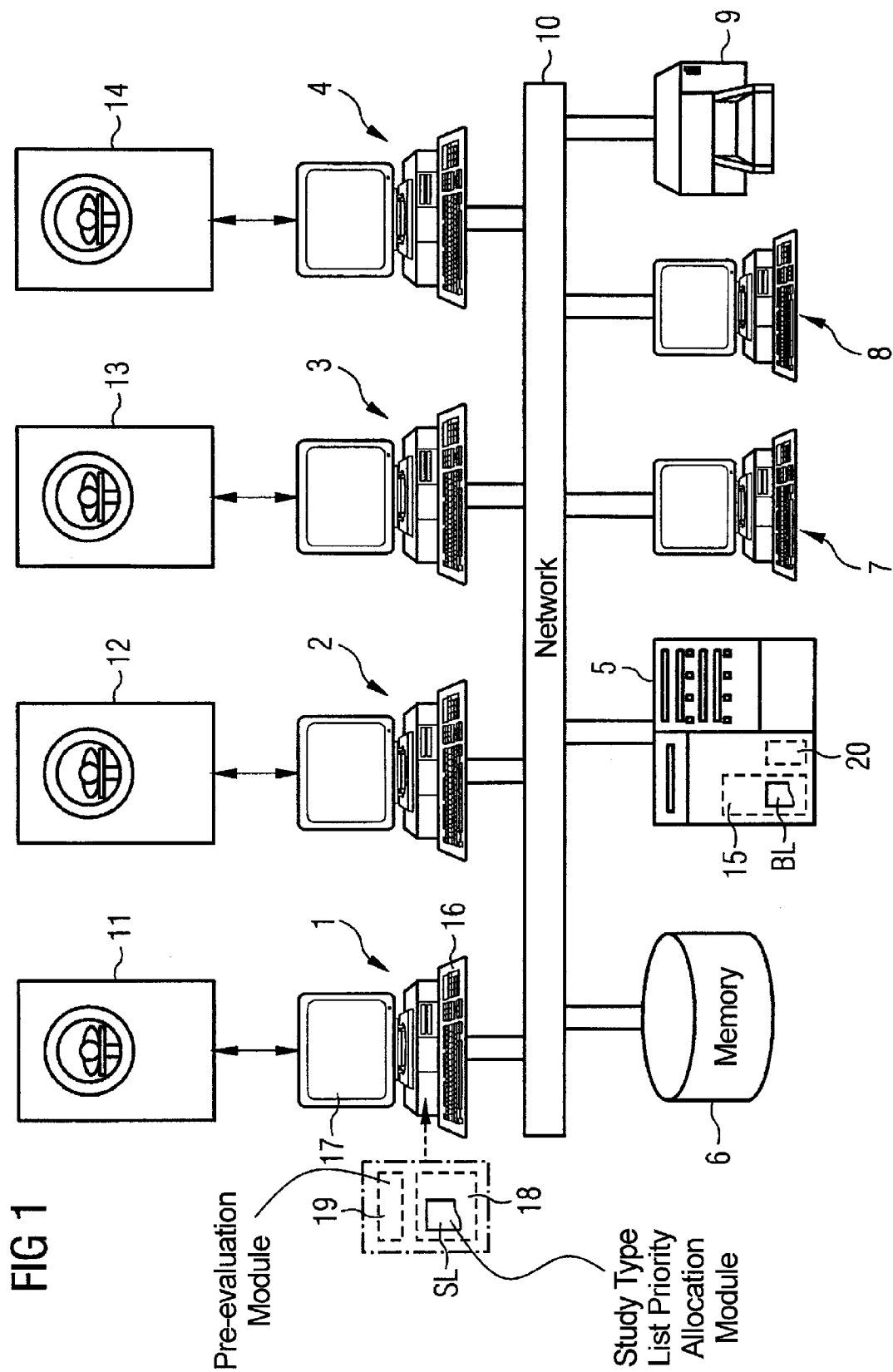

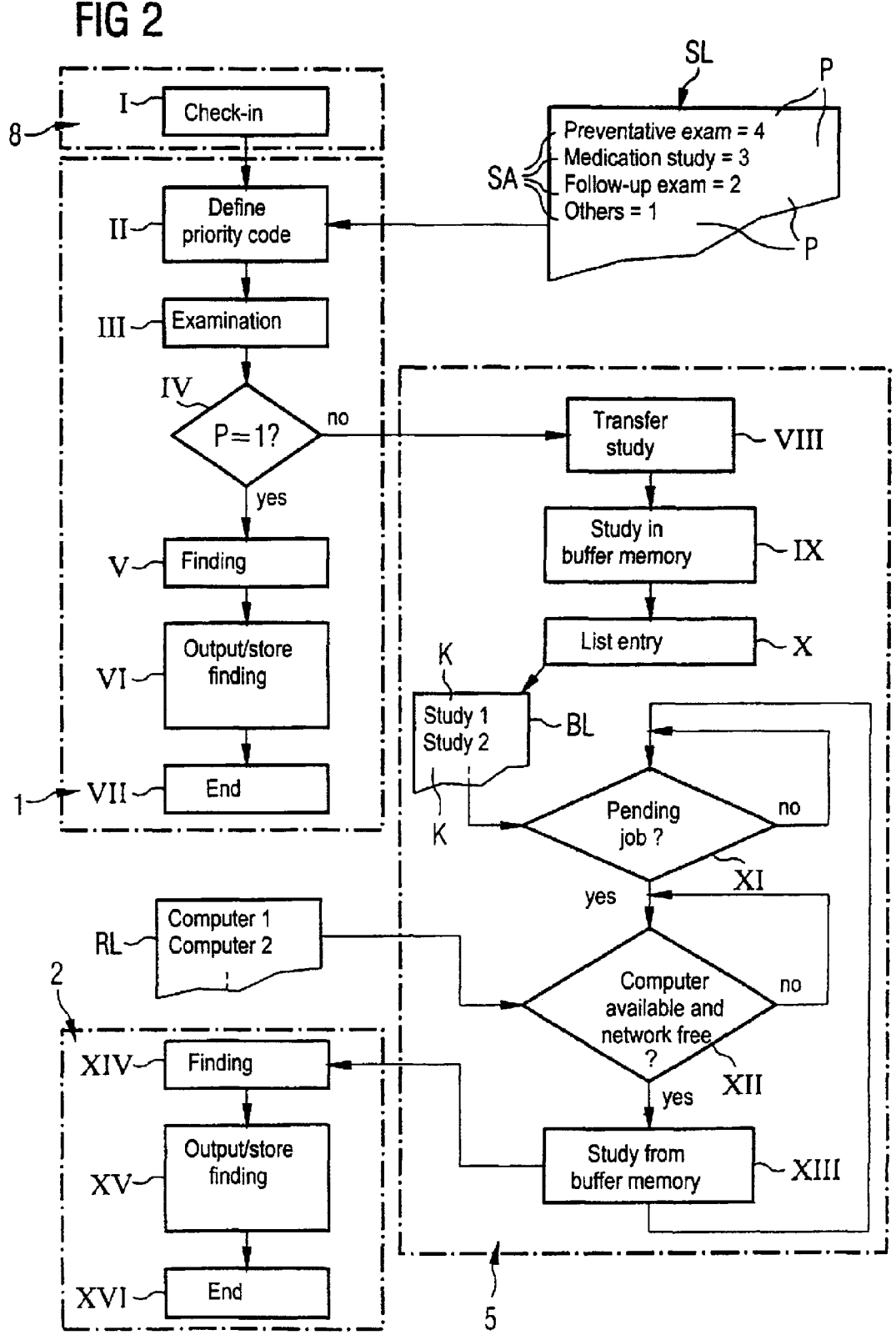

METHOD AND COMPUTERIZED SYSTEM FOR AUTOMATICALLY PROCESSING STUDIES ACQUIRED BY AN IMAGING EXAMINATION SYSTEM

BACKGROUND OF THE INVENTION

1. Field of the Invention

The present invention is directed to a method for automatically processing studies acquired by an imaging examination system as well as to a corresponding computerized system for the implementation of such a method.

2. Description of the Prior Art

A number of diseases can be recognized early and treatment measures initiated in time with the assistance of modem imaging examination systems such as, for example, magnetic resonance tomography systems, computer tomography systems, X-ray devices or ultrasound devices. Particularly pathologies such as coronary heart diseases, lung cancer or colon cancer, which are among the most frequent causes of death in the industrialized world, often can already be detected in a very early stage especially with tomographic examination methods such as magnetic resonance tomography or X-ray computed tomography. Regular preventative examinations even of non-symptomatic persons with such methods therefore could certainly considerably improve the chances of curing these diseases. Unfortunately, however, such examinations involve relatively high costs. Among the reasons for these high costs are the very large quantities of image data that arise as well as the time that is required for a finding by a radiologist. Dependent on the type of examination, for example dependent on whether it is a simple examination or a comparative examination with and without administration of contrast agent, one or more measurement series, referred to as studies, are acquired for an examination of a patient. Each of these studios is composed of at least one image, and usually is composed of a number of images from various slices of the examination subject. It can be assumed in a rough estimate that image that, for example, are stored in the DICOM standard (Digital Imaging and Communication) and are composed of an image header, which contains the information about the patient, the exposure location, the exposure time, etc., and include of the gray scale information that represent the actual image, with a data volume of approximately 200 KB. Given the assumption that a total of 1800 images are to be acquired for a complete screening of a patient in a magnetic resonance tomography system given a body height of 1.80 m for the patient and one image per mm, one such examination leads to a data quantity of 360 MB. Dependent on the type of examination, it may be necessary under certain conditions to not only process these images themselves in order to perform a finding for the study; rather, but also the images may have to be compared, for example, to images of preceding studies from other examinations. The quantity of data and the required time are correspondingly increased. One solution for reducing the costs, particularly in screening examinations, would be to make findings in an automated manner. At least the required work time of the radiologist thus can be reduced, since the radiologist would only have to be available only in cases that seem to be critical and/or for a possible spot-check monitoring of the findings. In practice, methods and computer systems already exist for automatically processing studies of imaging examination systems, including a complete evaluation, i.e., for example, a finding of the studies.

One problem of such automatic processing or finding, however, is the high computing capacity required therefor, since computing methods for such radiological applications require a very large number of processor operations, i.e. computing operations, comparison operations or the like, as well as a very large number of data bank queries at different data banks, even on different computers. Particularly in the case of comparison to studies of earlier examinations, extremely large quantities of data must be loaded, for example from an archive server that contains the historical data. The required operations and the transport of the data quantities burden the appertaining computer as well as the network to which the computer and the archive server are connected to a significant extent. Given a number of automatic findings by a computer, in particular, there is the risk that current operation on the appertaining examination system also will be affected and the examination durations therefore will be lengthened. Particularly given examinations wherein a fast finding is necessary, for example given an examination of patients with a suspected cardiac infarction or stroke, this can lead to critical delays. Moreover, longer examination times are relatively uncomfortable for the patient. Finally, longer examination times lead to a lower workload for the relatively expensive examination systems, which again indirectly involves higher costs.

SUMMARY OF THE INVENTION

It is an object of the present invention to provide a method and an imaging system for automatically processing studies of imaging examination systems with which an economical, automatic evaluation of the studies is possible and disadvantages thereby do not arise for applications that require fast answers.

In terms of the method, this object is achieved by allocating a priority code allocated to the studies acquired by an imaging examination system and, dependent on the priority code, the appertaining study is either processed immediately on a first computer allocated to the appertaining imaging examination system or the study (or the image data and other data of this study) is first intermediately stored in a memory device for a later processing, and an identifier allocated to the study is there by stored in a processing jot list. At later points in time, the studies with identifiers stored in the processing job list are processed according to a predefined sequence. The first computer has further computers allocated to it that are connected to the first computer via a network, and the availability of the allocated, further computers is checked and—insofar as one of the allocated computers is available for a processing of the study—an intermediately stored study is communicated to the appertaining, allocated computer, which receives and automatically processes the study.

The allocated, first computer can be, for example, the host computer of the examination system itself, for example an MR scanner. It can also be a central computer of a clinic system or of a practice system that is usually responsible for the processing of the studies of this imaging examination system.

The identifier can be an arbitrary data string or dataset that allows the identification of the study intermediately stored in the memory device, i.e. the image data and other data stored thereat that belong to the study. For example, this can be an identification number and/or the name of the patient, the date of the exposure or the examination device. The processing job list then contains this identifier, possibly in common with the priority code, in a form that allows the coordination of the processing of the individual studies. Such a processing job list can be implemented such that a newly added study or the identifier thereof is attached to the end of the list and the priority code also may be attached. A sorting according to priority codes also can ensue, or a number of partial lists for studies with different priority codes can be maintained. In this respect, the term "processing job list" also includes a data bank that allows a corresponding supervision and administration of the processing jobs that are still pending. The processing job list can be supervised by the first computer itself, or by a second computer connected thereto, for example by a central computer of a clinic system or practice system.

The sequence of the processing of the studies whose identifiers are stored in the processing job list can be prescribed dependent on the local conditions and requirements. The processing preferably ensues taking the allocated priority codes into consideration and otherwise ensues in sequence, i.e. based on how old the acquisition time of the study is.

The availability check wherein a determination is made as to whether an allocated, further computer is available for processing a study, preferably includes not only the check as to whether a corresponding computer with the required capacity is activated at all and can accept data but also includes a workload check of the allocated computer.

The implementation of this method requires a computer system that at least includes a first computer connected to an imaging examination system, a number of further computers that are allocated to the first computer and connected to one another as well as to the first computer via a network, as well as priority allocation unit for allocating a priority code to a study acquired by the imaging examination system. The first computer and the allocated computers must include means for the automatic processing of studies of imaging examination systems. The first computer must also be fashioned such that the study is immediately processed on that computer given certain priority codes and such that the study is otherwise deposited in a memory device. At least one of the computers belonging to the computer network—this can be the first computer itself or a further computer, for example a central computer—must include means for storing an identifier allocated to the appertaining study in a processing job list for the studies stored in the memory device and for initiating processing of the studies. This is undertaken by checking the availability of the allocated computers and communicating of an intermediately stored study to the appertaining, allocated computer, ensues insofar as one of the allocated computers is available for processing a study.

The allocated computers can be arbitrary computers that are available via the network, for example a hospital or practice Intranet or the Internet, either at a specific, current point in time, regularly at defined times, for example always at night, or are available for outsourced computing jobs. In particular, these can be computers that are respectively allocated to specific imaging examination systems and usually process the studies that were acquired on their "own" imaging examination systems. Insofar as these computers have no data to process from the imaging examination system that is allocated to them, they are fundamentally available for processing other computing jobs.

If as the network is a matter of a larger network, for example an intranet of a chain of practices or of clinics connected to one another, or the Internet, it is also possible for the various practices or clinics that are connected to the network to make computing capacities that are not currently needed available to one another.

The priority code of the study can already be entered by the examining personnel when a patient checks in for an examination, To this end, the priority allocation means must include a user interface for the entry of a priority code for a specific study or for a complete examination composed of a number of studies, so that this priority code is then assigned to the individual studies.

In an alternative, preferred exemplary embodiment, the priority codes are automatically assigned dependent on the study. To this end, for example, the priority allocation means can include a memory with a list of study types, each having a priority code is assigned thereto. The term "study type" as used herein defines the purpose for which the study is implemented, i.e. the priority is defined by the formulation of the reason for the examination. For example, it must usually be assumed that a very high priority is established for examinations due to a suspected cardiac infarction or stroke or similar acute problems, since an immediate processing of such a study must ensue. In contrast, follow-up examinations for confirming earlier examinations or for monitoring the progress of tumor patients, etc., should have a medium priority, so that results are available within a few days. Mere screening examinations for non-symptomatic patients, in contrast, can be processed with a low priority since the time until the finding is produced following the examination is usually not critical.

In a preferred method, an automatic pre-evaluation of at least a part of the study, for example of some of the images or of an individual overview image such as, for example a tomogram in a CT examination, ensues first. A priority code is then assigned dependent on pre-evaluation data of the study that are thus determined. Such a pre-evaluation also can ensue even if a priority code already was previously assigned. A new priority code is then assigned insofar as necessary on the basis of the pre-evaluation data that are determined One example of this is a very brief pre-evaluation of purely preventative studies requiring only little calculating time in order to determine whether an indication of an anomaly can be found in the evaluated part of the study. The study is provided with a higher priority and completely processed correspondingly faster only when such anomalies are indicated within the evaluated material. For example, an analysis of the appertaining image or of the image series in view of specific features and/or the transgression of certain defined limit Values, for example a maximum grayscale value within or in a specific region of the image that could indicate pathological changes, can ensue in the pre-evaluation.

A requirement for this purpose is that the computer system—preferably the first computer that is allocated to the imaging examination system—include a pre-evaluation device that first implements the automatic pre-evaluation of at least a part of the study and communicates the pre-evaluation data that are thereby determined to the priority allocation unit. The priority allocation unit must assign a priority code dependent on the pre-evaluation data of the appertaining study, or re-assign a priority code insofar as necessary if a priority code was already assigned. This pre-evaluation device preferably has a corresponding image processing unit for the implementation of a feature analysis.

In order to check the availability of the allocated computers, the workload of the processors or of the CPUs of the allocated further computers is preferably interrogated at regular time intervals. Classification can be made, for example, according to workloads of below 10%, below 50% and above 50%. Insofar as the workload lies below 10%, this is interpreted as the standby mode of the appertaining computer. A workload below 50% is considered light and a workload above 50% is considered heavy. Studies then are sent only to no-load computers or computers with a light workload, with no-load computers being used with priority.

The outsourced job orders are then processed on the respective computers with a low absolute priority, so that it is assured that local work processes that may arise are not impeded.

To avoid the network from being too heavily loaded by unnecessary data transmission, the traffic load of the network is measured, preferably at regular time intervals and/or before a transmission. A transmission of the study to the allocated computer then ensues only when the network traffic load does not exceed a predefined threshold. To this end, the computer system must have a unit for measuring the traffic load of the network.

The computer system preferably has a central computer that supervises the processing job list and checks the traffic load of the network as warranted and that initiates the transmission of an intermediately stored study to an available computer. It is assured in this way that the distribution of the jobs occurs in as coordinated a manner as possible to the available computer capacities.

It is also possible for the individual computers allocated to the various imaging examination systems to talk to one another and "lend" computing time to one another insofar as their capacities are not fully utilized. In this case, as well, however, one of the computers preferably assumes the supervision of the processing job list and thus assures the coordination.

It is meaningful that interrelated studies are also processed in common with the same priority, preferably on the same computer at the same time, or successively. These include, for example, studies that belong to one examination or to various examinations of the same patient or that belong together as comparative examinations, for example for medication studies.

DESCRIPTION OF THE DRAWINGS

FIG. 1 is a schematic illustration of an inventive computer system.

FIG. 2 is a flowchart of an embodiment of a sequence from the patient admission through the processing of a study according to the inventive method.

DESCRIPTION OF THE PREFERRED EMBODIMENTS

The computer system shown in FIG. 1 includes a total of four imaging examination systems 11, 12, 13, 14, also referred to as modalities below, that are each directly connected to an allocated computer 1, 2, 3, 4. These computers 1, 2, 3, 4 serve for driving of the respective modalities 11, 12, 13, 14 and for processing the studies generated by the modalities 11, 12, 13, 14, particularly for evaluation or findings thereof. The individual computers 1, 2, 3, 4 of the modalities 11, 12, 13, 14 are respectively connected to one another via a network 10, for example a bus system.

A memory 6 for storing and archiving the studies also is connected to the network 10. Further, a central computer 5 is connected to the network 10, the central computer 5 serving as a network server and likewise making computer capacities available for processing studies. This central computer 5 also serves for the administration of the memory 6 in the exemplary embodiment.

Moreover, picture screen workstations 7, 8, for example in the form of PCs or workstations, are connected to the network 10, these likewise allowing a processing of image data, especially a sorting or finding by operating personal and, for example, also being able to be used for the check-in of a patient before an examination.

The patient data that are entered at such a picture screen workstation 7, 8 are communicated via the network 10 to the computer 1, 2, 3, 4 that is responsible for the modality 11, 12, 13, 14 at which the respective patient is to be examined. Moreover, the data also may be handed over to the network server 5 and deposited in the memory 6 of the system.

Finally, a printer 9 is connected to the network 10 for printing out patient data as well as examination results such as, for example, images or findings.

It should be noted that the illustrated network 10 is only an exemplary embodiment and that a network for the implementation of the inventive method can have a completely different architecture. For example, a number of modalities can be allocated to a shared computer. Likewise, the modalities can be directly connected to the network and communicate with the respectively allocated computer via the network. Further, it is also possible for an individual modality to be directly allocated to multiple computers that are specifically provided for processing the data of this modality. It is also clear that considerably more or fewer modalities can be connected to the network. Likewise, a number of different memory devices as well as a number of mainframe computers and a higher number of image workstations and printers can be connected to the network. In particular, it is also possible for the network to be connected to a larger network, for example the Internet, via a corresponding interface and thus in turn can be connected to further computers or local networks.

All standards suitable for radiological information systems (RIS) or for image information systems (PACS, Picture Archiving and Communication System) such as, for example, the standards OSI, TCP/IP, DICOM and IPI often employed in radiological information systems, can be employed for the communication of the images and the administrative data for the examination of patients.

The tasks of the individual components are explained below with reference to an exemplary embodiment on the basis of the flowchart in FIG. 2. This flowchart shows the method sequence from the check-in of the patient through the processing of a study generated in an examination of the patient. This is a method execution that is implemented on various components connected to the network 10.

The method begins in method step I with the check-in of the patient, for example at one of the picture screen workstations 8. The personal data of the patient are recorded at this picture screen work station 8, and the examination that is to be implemented is specified, for example an acute examination, a follow-up examination or a screening examination. Such data are then communicated to a computer 1 that is allocated to the modality 11 that is provided and reserved for the examination. At the same time, the patient receives the instruction to report to this modality 11, a magnetic resonance tomograph here, whereupon the patient goes to that location.

In addition to the standard tasks that are then handled on the allocated first computer 1 of the modality 11 before an examination, a priority code P is also defined. This can ensue by input by the personnel with the user interface of the first computer 1 composed of a keyboard 16 and a picture screen 17. The definition of the priority code P, however, preferably already ensues automatically in a priority allocation module 18 that is realized in the form of software on the appertaining computer 1.

This priority allocation module 18 contains a study type list SL in which various priority codes P are defined for various study types SA (or examination types). Screening examinations of non-symptomatic patients are thus assigned the priority code "4", examinations of medication studies a priority code "3", follow-up examinations for monitoring tumor patients the priority code "2" and other types of studies the priority code "1". Here, "1" represents the highest priority that demands an immediate processing of the studies. These therefore include all acute examinations that are not explicitly referenced in the study list SL. In this respect, the study type list SL contains only an exclusion list of examinations for which an immediate processing of the studies generated in the examination is usually not initially required.

The priority allocation module 18 then automatically determines the type of study involved and assigns the priority code P in conformity therewith. Alternatively, it is also possible that the priority allocation is already implemented—either manually or automatically on the basis of the study type—at the picture screen work station 8 at which the patient check-in ensued.

After the priority code has been determined in method step II, the examination then ensues in method step III.

Subsequently, a check is made in method step IV to determine whether a priority code P is present that requires an immediate processing of the study, a priority code "1" here. When this is the case, then the study is immediately processed in method steps V and VI, whereby a finding occurs first in method stop V and the finding is output and/or stored in method step VI. The storage of the finding within the memory 6 preferably ensues in common with the appertaining administrative data and the image data of the patient produced in the study, For example, the output of the finding can ensue at the picture screen 17 of the computer 1 and/or via the printer 9. Subsequently, the procedure is ended in method step VII.

When, in contrast, it is found in method step IV that the priority code P in the present case is not "1", i.e. an immediate processing is not needed. then the study is handed over to the central computer 5 in method step VIII, which first causes an intermediate storage of the study in the memory 6 in the following methods step IX. Moreover, an identifier K with which the study can be unambiguously identified, is entered into a processing job list BL in method step X.

In an alternative embodiment not shown in FIG. 2, a relatively short pre-evaluation that requires only little computing time is also initially implemented in a pre-evaluation module 19 realized in the form of software on the first computer 1 for specific studies with a lower priority, for example mere preventative studies, in order to determine whether an indication that an anomaly may be found in the evaluated part of the study. When such anomalies are indicated within the pre-evaluated material, the study is subsequently provided with a priority code of "1" and, accordingly, is immediately completely processed.

The intermediately stored studies, the respective identifier K of which are stored in the processing job list BL, are then processed in the following way:

In method step XI, the central computer 5 regularly checks whether a pending job is present in the job order list BL.

When this is the case, then a check is made in method step XII to determine whether a computer is available and whether the network 10 is overloaded. For checking the availability, the central computer 5 checks the workload of the CPUs of all allocated computers 2, 3, 4 available for a processing of studies at regular time intervals. It can also additionally take into consideration the first computer 1 from which the appertaining job originally came and also allocate a work job to it insofar is it does not have a full workload at a later point in time. The central computer 5 preferably is likewise equipped with means to automatically process studies, i.e., it can itself process studies pending in the processing job list insofar as it does not have too heavy a workload.

The workload of the computers is classified into three categories. It is assumed below a 10% workload that the respectively computer has no load and, for example, is in a standby mode. A low workload is assumed given less than 1 50% workload and a high workload is assumed given a workload of more than 50%.

The check of the availability and the monitoring of the processing job list BL ensues with the assistance of a job monitoring module 15 that is implemented on the central computer 5 in the form of suitable software. The computers that can be fundamentally available for processing studies, i.e. the allocated computers, are presented to the central computer 5 in a computer list RL. Insofar as the network is expanded, it is merely necessary to enter this newly added computer in the computer list RL.

The network occupancy, i.e. the performance of the network 10, can be checked in a relatively simple way, for example, by the central computer 5 sending a test signal to a further computer component connected to the network 10, this further computer component replying to this test signal. When measures are implemented to insure that the reaction time of the replying computer component is itself relatively short, then the time until receipt of the reply signal at the central computer 5 is mainly dependent only on the occupancy of the network 10. For this reason, the test signal to be answered is preferably sent to a component that has only a low workload, for example to the printer 9. A typical example of a transmission of a signal to be answered is referred to as the 'ping' function in a Unix network. When the measured reply time lies above a certain threshold, then it is assumed that the network 10 is overloaded and no studies whatsoever are handed over from the memory 6 to the allocated computers for processing. This check of the network performance can ensue at regular time intervals—nearly permanently as well—or every time when a transmission of more extensive study data is planned. To this end, a network occupancy module 20 is implemented on the central computer 5 in the form of suitable software that collaborates with the job-monitoring module 15.

If it is found in method step XII according to FIG. 2 that a computer is available and that the network is not overloaded, a study from the buffer memory 6 is sent to the appertaining computer in method step XII, to a computer 2 allocated to a different modality 12 in this case. The computer 2 then implements the automatic finding in method step XIV. In method step XV, the finding is in turn output, for example at the printer 9, and stored in the memory 6. Subsequently, the processing is ended in method step XIV, and the appertaining computer 2 is available again for accepting further job orders from the central computer 5.

The job order assigned by the central computer is processed with only a relatively low absolute priority on the appertaining computer 2, so that a processing of jobs currently coming from its own modality 12 does not incur any time disadvantages.

The computer capacities of the entire computer system are optimally used by means of the inventive method without incurring delays in applications that require a fast reply time. In this way, the costs can be lowered, particularly for those examinations that are not time-critical such as, for example, preventative examinations, so that these can ultimately be financed to a greater extent as a preventative examination even for non-symptomatic persons. The invention, moreover, is not limited to employment in the medical field but also can be utilized in other fields where there is a demand for an automatic processing of studies of imaging examination systems such as, for example, in the case of materials inspection devices.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for automatically processing studies acquired by an imaging examination system having a first computer connected via a network to a plurality of further computers, said method comprising the steps of:

for each study in a plurality of studies, comprising study data, acquired by said imaging examination system, assigning a priority code indicating a relative priority for processing that study;

dependent on said priority code, either immediately processing said study on said first computer by automatically diagnostically analyzing the study data thereof in said first computer to produce a medical finding, or intermediately storing the study data of said study in a memory device for later processing of the study data and allocating respective identifiers, in a processing job list, to all studies stored in said memory and, at respective later points in time, processing the respective study data of the studies stored in the memory in said processing job list according to a predetermined sequence; and for processing the respective study data of the studies stored in said memory at said respective later points in time, checking respective availabilities of said further computers for processing one of said studies according to said processing job list, and communicating one of said studies according to said processing job list to one of said further computers having availability and automatically diagnostically analyzing the study data thereof in said one of said other computers having availability to produce a medical finding.

2. A method as claimed in claim 1 wherein the step of checking availability of said other computers comprises checking a workload of the respective other computers.

3. A method as claimed in claim 1 wherein each study has a study type associated therewith, and comprising allocating said priority code to the respective study dependent on the study type.

4. A method as claimed in claim 1 comprising, before assigning said priority code to a study, automatically pre-evaluating at least a portion of the study data of that study and assigning said priority code dependent on said pre-evaluation.

5. A method as claimed in claim 4 wherein said study data include an image comprising image features and at least one defined limit value, and wherein the step of pre-evaluating at least a part of the study comprises analyzing at least one of said image feature and said at least one defined limit value.

6. A method as claimed in claim 1 comprising the additional steps of monitoring an occupancy of said network and transmitting a study from said memory to said one of said other computers only if the occupancy of said network does not exceed a predetermined threshold.

7. A method as claimed in claim 1 comprising ordering said studies in said predefined sequence according to said priority codes.

8. A method as claimed in claim 1 wherein said network has a central computer connected thereto, and comprising the steps of administering said processing job list in said central computer by, in said central computer, checking the respective availabilities of said other computers and initiating transmission of said one of said studies from said memory to said one of said other computers having availability for processing the study data thereof.

9. A method as claimed in claim 8 comprising the additional step of, in said central computer, monitoring an occupancy of said network and transmitting said one of said studies from said memory to said one of said other computers only if said occupancy of the network does not exceed a predetermined threshold.

10. A method as claimed in claim 1 wherein said plurality of studies include interrelated studies, and comprising processing the respective study data said interrelated studies in common by automatically diagnostically analyzing the respective study data of said interrelated studies, either in said first computer or said one of said other computers dependent on the priority code of at least one said interrelated studies.

11. A computerized system for automatically processing studies acquired by an imaging examination system, said computerized system comprising:

a first computer connected to an imaging examination system that acquires a plurality of studies, each of said studies comprising study data;

a priority allocation module configured to allocate respective priority codes to said studies according to a relative processing priority;

a plurality of other computers in communication with said first computer, each of said first computer and said plurality of other computers comprising a processor configured to automatically process said studies by automatically diagnostically analyzing the study data thereof to produce a medical finding;

a memory accessible by said first computer and said other computers;

dependent on the priority code allocated to a study, either said first computer automatically analyzing the study data of that study or intermediately storing that study in said memory allocated to an identifier in a processing job list for all studies stored in said memory; and a module configured to check respective availabilities of said other computers and to transmit one of said studies from said memory according to said processing job list to one of said other computers dependent on the availability of said one of said other computers, for processing the study data thereof in said one of said other computes to produce a medical finding.

12. A computerized system as claimed in claim 11 wherein said module is configured to check the respective availabilities of the other computers by checking the respective workloads of the other computers.

13. A computerized system as claimed in claim 11 wherein said priority allocation module comprises a user interface allowing manual entry of respective priority codes for said plurality of studies.

14. A computerized system as claimed in claim 11 wherein said priority allocation module comprises a priority allocation memory containing a list of study types, and wherein said priority allocation module is configured to allocate said priority codes dependent on a study type of each study in said plurality of studies.

15. A computerized system as claimed in claim 11 wherein said first computer includes a pre-evaluation module configured to automatically implement, before allocation of said priority code by said priority allocation module, a pre-evaluation of at least a part of a study, thereby obtaining pre-evaluation data, and to communicate said pre-evaluation data to said priority allocation module, and wherein said priority allocation module to allocate a priority code to that study dependent on the pre-evaluation data for that study.

16. A computerized system as claimed in claim 15 wherein said pre-evaluation module comprises an image processing unit, configured to analyze features of an image associated with the study within the automatic diagnostic analysis of the study data of that study.

17. A computerized system as claimed in claim 11 wherein said first computer and said other computers are in communication via a network, and wherein said module for transmitting said one of said studies from said memory to said one of said other computers is configured to monitor an occupancy of said network and to transmit said one of said studies to said one of said other computers only if the occupancy of said network does not exceed a predetermined threshold.

18. A computerized system as claimed in claim 11 further comprising a central computer containing said module, said central computer being configured to said processing job list using said module.

19. A computerized system as claimed in claim 18 wherein said first computer and said other computers are in communication with each other via a network, and wherein said central computer is configured to monitor an occupancy of said network and to initiate transmission of said one of said studies to said one of said other computers only if the occupancy of the network does not exceed a predetermined threshold.

* * * * *